United States Patent
West

(10) Patent No.: US 6,646,062 B1
(45) Date of Patent: Nov. 11, 2003

(54) PRODUCTION OF IMPROVED POLYMERS VIA THE USE OF STAR CORES

(75) Inventor: Simon Michael West, Williamstown (AU)

(73) Assignee: Petrecycle Pty Ltd (AU)

( * ) Notice: Subject to any disclaimer, the term of this patent is extended or adjusted under 35 U.S.C. 154(b) by 0 days.

(21) Appl. No.: 09/787,676

(22) PCT Filed: Sep. 23, 1999

(86) PCT No.: PCT/AU99/00798

§ 371 (c)(1),
(2), (4) Date: Mar. 21, 2001

(87) PCT Pub. No.: WO00/17151

PCT Pub. Date: Mar. 30, 2000

(30) Foreign Application Priority Data

Sep. 23, 1998 (AU) .............................................. PP6107

(51) Int. Cl.⁷ ........................ C08G 63/91; C07C 53/12; C07C 63/331
(52) U.S. Cl. ........................ 525/437; 560/89; 562/887; 562/888; 562/895
(58) Field of Search ........................ 525/437; 562/887, 562/888, 895; 560/89

(56) References Cited

U.S. PATENT DOCUMENTS

| | | | |
|---|---|---|---|
| 3,962,190 A | 6/1976 | Wear | |
| 4,145,466 A * | 3/1979 | Leslie | 428/480 |
| 4,291,152 A | 9/1981 | Inata et al. | |
| 4,945,151 A * | 7/1990 | Goodley et al. | 528/272 |
| 5,034,502 A * | 7/1991 | Hirose et al. | 528/271 |
| 5,346,984 A | 9/1994 | Hasegawa et al. | |

FOREIGN PATENT DOCUMENTS

| | | |
|---|---|---|
| AU | A-10560/92 | 8/1992 |
| EP | 0 404 328 A2 A3 | 12/1990 |
| EP | 0 672 703 A1 | 9/1995 |
| JP | 53082743 * | 7/1978 |
| WO | WO 95/06081 A1 | 3/1995 |
| WO | WO 98/33837 * | 8/1998 |

OTHER PUBLICATIONS

Derwent Abstract Accession No. 61891A/35.
Merck Index Monograph No. 9832.
Derwent Abstract for JP 55013797 (XP002232238).

* cited by examiner

Primary Examiner—Patricia A. Short
(74) Attorney, Agent, or Firm—Townsend and Townsend and Crew LLP

(57) ABSTRACT

There is provided a process for producing high molecular weight polymer comprising the step of reacting one or more preformed linear polymers with one or more cores (as hereinbefore defined) to form high molecular weight polymers, wherein the preformed linear polymers are at a temperature in the range from the melting point of the preformed linear polymers to 330° C.

9 Claims, No Drawings

PRODUCTION OF IMPROVED POLYMERS VIA THE USE OF STAR CORES

FIELD OF THE INVENTION

The invention relates to a process for producing high molecular weight polymers.

The invention also relates to star cores which may be used in the production of the above polymers. More particularly, the star cores are bi-functional ("I"), tri-functional ("Y") and tetra-functional ("H") polymer cores.

BACKGROUND TO THE INVENTION

It will be appreciated that whilst the following specific description refers to polyester polymers and applications of these to stretch blow moulding, the invention is not so limited.

It is now the practice to produce high molecular weight polymer as a melt of intrinsic viscosity about 0.6 dl/g, then extrude and freeze the product to give pellets that are further polymerised by solid state polymerisation to give intrinsic viscosity of 0.8 dl/g for stretch blow moulding and 1.0 dl/g for high tenacity fibre for tyre cord. The pellets are melted and then formed. It is recognised that production of suitable weight average molecular weight in the original melt, followed by immediate use of the molten polymer would avoid the costly intermediate steps currently employed with further processing and has the potential to save time and energy and considerable cost.

Similarly, the desire to be able to convert polymers with a low weight average molecular weight into a polymer with a high weight average molecular weight has also been recognised as highly advantageous in, for example, fibre production.

In order for a polyethylene terephthalate ("PET") polymer to be stretch blow moulded it must have a relatively high weight average molecular weight and sufficient intrinsic viscosity. A table linking the intrinsic viscosity with the Mw is set out in Table 1. One of the prime difficulties in producing a PET polymer polymer has been the production of a polymer with sufficient weight average molecular weight. The weight average molecular weight (Mw) of a polymer chain can be calculated as follows:

$$avMw = \Sigma Mi^2/\Sigma Mi$$

where Mi is the individual polymer molecular weight.

TABLE 1

Weight Average Molecular Weights versus Intrinsic Viscosity dl/g

| | |
|---|---|
| IV-0.6 | Mw = 33600 |
| IV = 0.61 | Mw = 34400 |
| IV = 0.62 | Mw = 35300 |
| IV = 0.63 | Mw = 36200 |
| IV = 0.64 | Mw = 37000 |
| IV = 0.65 | Mw = 37900 |
| IV = 0.66 | Mw = 38800 |
| IV = 0.67 | Mw = 39700 |
| IV = 0.68 | Mw = 40600 |
| IV = 0.69 | Mw = 41500 |
| IV = 0.7 | Mw = 42400 |
| IV = 0.71 | Mw = 43400 |
| IV = 0.72 | Mw = 44300 |
| IV = 0.73 | Mw = 45200 |
| IV = 0.74 | Mw = 46200 |

TABLE 1-continued

Weight Average Molecular Weights versus Intrinsic Viscosity dl/g

| | |
|---|---|
| IV = 0.75 | Mw = 47100 |
| IV = 0.76 | Mw = 48100 |
| IV = 0.77 | Mw = 49100 |
| IV = 0.78 | Mw = 50000 |
| IV = 0.79 | Mw = 51000 |
| IV = 0.8 | Mw = 52000 |
| IV = 0.81 | Mw = 53000 |
| IV = 0.82 | Mw = 54000 |
| IV = 0.83 | Mw = 55000 |
| IV = 0.84 | Mw = 56000 |
| IV = 0.85 | Mw = 57000 |
| IV = 0.86 | Mw = 58000 |
| IV = 0.87 | Mw = 59000 |
| IV = 0.88 | Mw = 60100 |
| IV = 0.89 | Mw = 61100 |
| IV = 0.9 | Mw = 62200 |
| IV = 0.91 | Mw = 63200 |
| IV = 0.92 | Mw = 64300 |
| IV = 0.93 | Mw = 65400 |
| IV = 0.94 | Mw = 66400 |
| IV = 0.95 | Mw = 67500 |
| IV = 0.96 | Mw = 68600 |
| IV = 0.97 | Mw = 69700 |
| IV = 0.98 | Mw = 70800 |
| IV = 0.99 | Mw = 71900 |
| IV = 1. | Mw = 73000 |

From a theoretical perspective, in order for a PET polymer to be capable of being stretch blow moulded it must have an intrinsic viscosity in the range of 0.7 to 0.8 dl/g. The viscosity can be determined if the weight average molecular weight of the polymer chain is known since the logarithm of the melt viscosity is related to the square root of the weight average molecular weight of the polymer chain. The equation for melt viscosity is:

$$\log(n) = \text{constant} * \sqrt{(avMw)}$$

where n is viscosity and Mw is weight average molecular weight. Thus the technically important flow characteristics required during stretch blow moulding (such as injection moulding) are dependent on the weight average molecular weight.

Even where a sufficient Mw is achieved, another substantial problem in polymers has been the tendency during polymerization of the polymer to gel. During uncontrolled polymerization the random cross-linking and branching reactions that occur result in gelled products due to the highly branched structures. Such polymer structures are unsuitable for stretch blow moulding or fibre production. It has been recognised that polymers suitable for stretch blow moulding should have a small change in viscosity when the shear is changed and this property is found in linear polymers. In contrast, polymers containing polymers with many randomly spaced branches are gel-like and do not have this property.

Accordingly, investigations were conducted to develop a process to prepare polymers that have controlled degrees of branching and have a central core attaching linear chains and polymers with multifunctional centres or cores to which linear polymers preferentially attach.

It is known from the prior art that linear polymers may be altered to so-called star polymers by using small proportions of polyfunctional additives which form the "core" of the star polymer and allow linear polymers to attach thus increasing the weight average molecular weight of the resulting polymer. There is a considerable body of knowledge of these star polymers that allows the properties of a given preparation of polymer to be anticipated (for example, J. R. Schaefgen & P. J. Flory; J. Am. Chem. Soc. 70,2709,1948 "Schaefgen"). The processes in the prior art use substances that are thermally unstable, expensive and produce yellow by-products, and further these processes produce products with gel branching.

Schaefgen discloses very early research in the use of star polymers. This research explored the use of polyamines and polybasic acids (such as polyacrylic acid) however, no commercially useful products were produced. Schaefgen while describing the theoretical basis of star polymers and correctly anticipating the problems does not give any practical solutions. Moreover, Schaefgen is not directed to the formation of PET polymers which have unique problems because being ester polymers, it is difficult to develop appropriate polyfunctional compounds.

The use of polyfunctional cores is also disclosed in U.S. Pat. Nos. 3,692,744, 3,714,125 and 3,673,139.

In U.S. Pat. No. 3,673,139, the increased viscosity and gummy elasticity of polyesters due to the increasing degrees of cross-linking or branching was recognised and sought to be addressed by condensing during the processing of the polymer, 0.001 to 1 mol % of a compound having not less than three polyester forming functional groups so as to form slightly branched or cross-linked polyesters with an intrinsic viscosity of at least 0.8 dl/g or preferably 0.9 dl/g and a substance which promotes crystallisation. The process disclosed is a reaction of terephthalic acid ester, ethylene glycol and the polyester forming group. The products of this process are unsatisfactory as they do not meet the required colour and linear viscosity characteristic with the low addition rate described.

U.S. Pat. No. 3,692,744 discloses the inclusion in a poly-esterification mixture, in addition to a terephthalic acid component and a diol component, of 0.05–3 moles percent of the acid component of a compound containing at least 3, preferably 3–4, ester forming groups (for example, a tri- or tetra-carboxylic acid, a triol or tetrol or a hydroxy carboxylic acid containing in all 3 or more ester-forming groups). Again, the methods disclosed in this art provide for the addition of the polyfunctional compound as a starting material. This patent discloses the use of triols and tetraols that are unsuitable because the substances are unstable and at temperatures higher than about 290° C. dehydrate to give a double carbon bond which produces coloured by-products.

A substantially "+" shaped polyfunctional centre or core is disclosed in U.S. Pat. No. 3,714,125 being an aromatic ortho-carbonate. These substances are highly unstable in melts and would, for example, be unsuitable for clear soft drink bottles.

It is also known that as the number of carboxylic acid groups on an aromatic ring are increased, the rate of decomposition to give carbon dioxide is increased in proportion to the number of such substituents. Accordingly, when four or more carboxylic acid groups are present then one or more is rapidly lost to generate carbon dioxide. Such substances are difficult to prepare and production has ceased because the substances are carcinogenic and too costly to produce.

All of the polyfunctional additives or multifunctional cores that have been used in star polymer technology to date suffer from considerable disadvantages. Although the choice of polyfunctional additives that have been used to date have attempted to control random cross-linking or branching during polymerisation, the polymers produced continue to suffer from unacceptable levels of gel which do not allow the products to be commercially useful for stretch blow-moulding. In some cases, the prior art polymers also have insufficient weight average molecular weights and/or intrinsic viscosity to be useful, particularly where the stars have only one functional core.

Further in each of the known processes, commercially unacceptable star polymer products are produced as a result of the continued gelation and coloured by-products which render the products unsuitable to be used, for example, for clear beverage bottles.

Therefore, there is a need for a process for producing star polymers which are commercially useful, especially in the production of PET bottles.

SUMMARY OF THE INVENTION

Throughout this specification and in the claims, the word "core" will be understood to mean a compact molecule with more than one reactive group that is relatively stable under the conditions of use. This is because the core does not react with the constituents of the polymer melt.

Throughout this specification and in the claims, the word "preformed" is used to indicate that there is formation of long chain linear polymers prior to the use of any star core additives.

According to the invention there is provided a process for producing high molecular weight polyesters comprising the step of reacting one or more preformed linear polymers with one or more cores (as hereinbefore defined) to form high molecular weight polysters; wherein the preformed linear polymers are at a temperature in the range from the melting point of the preformed linear polymers to 330° C.

The pressure under which the reaction occurs is not critical. Preferably, the reaction is performed under vacuum to maximise removal of by-products such as ethanediol and acetic acid.

Preferably, the preformed linear polymers are at a temperature of at least about 270° C. More preferably, the preformed linear polymers are at a temperature of about 280° C.

Preferably, the reaction occurs for a period of time of less than tern minutes. It is necessary to limit the reaction time to maximise the reactions of the core with long chain linear polymers and avoid the formation of an equilibrium.

The preformed linear polymers can be prepared using any of the methods known to those skilled in the art.

Preferably, the cores used to link the polymers are in the form of a mixed anhydride as these cores provide particularly fast routes to the production of high molecular weight polymers. More preferably, the mixed anhydride is the acetic acid anhydride of isophthalic acid.

Preferably, the star cores are selected from the group consisting of star cores of the general "H", "Y" or "I" forms discussed below, trimellitic acid, trimellitic anhydride or mixtures thereof.

According to the invention, it is possible to set a target for the Mw of the finished product and to choose a starting material with an appropriate Mw. The starting material can be a commercially available product. For example, low Mw polymers may be purchased economically and then by using the simple process of this invention, converted to high Mw polymer which may have the suitability to be, for example, stretch blow moulded. Packaging manufacturers can therefore easily obtain high Mw polymer and then extrude the polymer to make, for example, soft drink bottles. The intrinsic viscosity of the starting material can be predetermined by the processes used to form it.

Preferably, the preformed linear polymers are polyester polymers. In preferred forms of the invention, the polyester polymer is preferably selected from the group including PET, polybutylene terephthalate and polyethylene naphthenates. More preferable, the polyester polymer is PET. Where the polymer is PET, it may be formed by, for example, reacting terephthalic acid with ethanediol to form PET polymer having an intrinsic viscosity of between 0.7 dl/g and 0.8 dl/g.

It has further been found that by using this process, PET polymers may be formed with a predetermined defined weight average molecular weights and with no detectable change of colour.

In this way, the resultant weight average molecular weight can be improved by initially forming the linear PET polymers and then growing the polymers onto the star core. This enables the amount of star core to be added to be determined with statistical accuracy. The ability to calculate the required amounts of star core based on the pre-formed linear polymers allows for this process to be commercially valuable.

The PET ester polymers produced according to the invention are preferably capable of being stretch blow moulded. To this end, it will be understood by persons skilled in this art that this invention allows the solid state polymerisation step of, for example, basic polyethylene terephthalate processing to be eliminated and that direct injection moulding of the product is feasible to produce a useful polymer for soft drink bottles and other applications. This invention thus allows a significant reduction in the cost of production of useful polymer.

It will be understood that the invention includes polyester polymers (such as PET ester polymers) when produced by the processes of the invention. It will be further understood that the invention includes a process for producing stretch blow moulded products using polyester polymers (such as PET polymer) which has been produced by the methods of this invention and further stretch blow moulded products when produced by such a process.

It has also been found that by using cores of a general "I", "H" and/or "Y" form, polymers can be produced which have a weight average molecular weight within a defined range which allows such polymers to become more commercially useful, eg in stretch blow moulding or fibre production.

According to a second aspect of the invention, there is provided star cores for use in the preparation of high molecular weight polymer selected from the group consisting of compounds of the general "H" form:

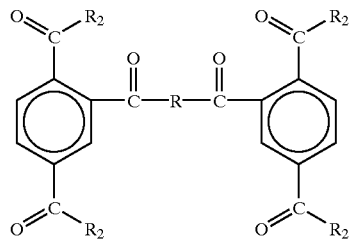

$R_2$ is —OH, —O—CO—CH$_3$, —OCH$_2$CH$_2$OH wherein R is

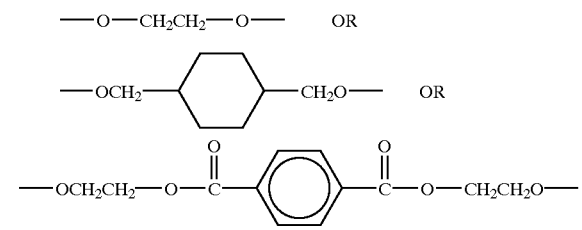

compounds of the general "Y" form:

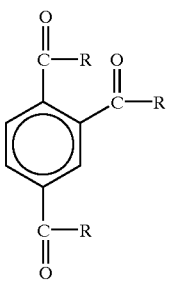

where R is —OCOCH$_3$ or —OCH$_2$CH$_2$OH and compounds of the general "I" form:

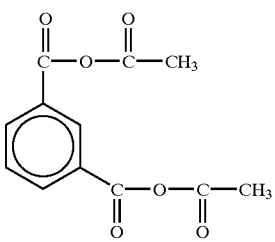

or mixtures thereof.

The star cores can be in the free carboxylic acid form or an active form, that is, a mixed anhydride or an ester (eg with ethanediol). The mixed anhydride form of the invention is preferred because it has been shown to be the most efficient star core with superior results being obtained very quickly. In particular, they allow the production of a variety of different molecular weight distributions with high average Mw rapidly and without significant colour problems. The mixed anhydride does not rely on transesterification, which is intrinsically slow, but instead relies on the fast reaction of mixed anhydrides with free terminal hydroxyl groups. Therefore, examples of the tri-functional "Y" core include trimellitic anhydride, trimellitic acetic anhydride or tris hydroxyethyl trimellitate.

When the "I" core is used, the addition of the core causes simple linking of the polymer chains. It was found that isophthalic acid would form useful derivatives but terephthalic acid would not. "I" cores give rapid linkage of the terminal hydroxyl groups to give linear polymers with a "bend" due to the substitution of isophthalic acid for terephthalic acid.

Preferably, there is provided star cores of the "I", "H" and "Y" form of the formulae described above for use in processes for forming polyester polymers (such as polyethylene terephthalate ("PET") polymers) having a general "I", "H" or "Y" form respectively. It has been found that the optimal viscosity of the polymers may be found by the addition of the "H" core during the last stage of polycondensation, because the minimum quantity of crossbar is converted to simple tri-star polymer by transesterification of the crossbar. It is believed that the transesterification reaction in the polymer production means that the connecting ester bonds of the H core are also possibly attacked resulting in conversion to the Y core form. Of course, this may be a preferred process, if predominantly "Y" star polymer is desirable. Obviously, as this is a statistical process, delaying the addition reduces the proportion of conversion to the Y form, if the H form is preferred.

Star cores of these "I", "H" and "Y" forms have the structure and reactive groups to enable them to be used to produce polyester polymers (particularly, PET polymers) which have improved characteristics. Namely, the polyester polymers produced are of a sufficient weight average molecular weight to enable them to be stretch blow moulded and can be produced without creating coloured by-products.

In particular, according to the process of this invention, the linear properties and ease of manufacture of the "I", "H" and "Y" PET polymers may be enhanced markedly by delaying the addition of the core until sufficient polymerisation has occurred for the core to subsequently react with linear polymers and give the required polymer properties. The delayed addition is not essential and improved polymers can of course be achieved by, for example, the early addition of the core(s). For example, very high reaction rates can be achieved using the mixed anhydride forms of the invention. This reaction is promoted by the use of, for example, the mixed anhydride cores to target terminal hydroxyl groups without the undesirable side reaction of ethanediol released then attacking and breaking existing long linear chains.

DESCRIPTION OF THE PROCESS FOR THE PRODUCTION OF STAR CORES

The processes used to produce the star cores of this invention will now be described in further detail followed by examples of their production.

The star cores of this invention can be produced in several ways.

From the above structures, it will be appreciated that the "Y" star cores can be constructed using one trifunctional element and the "H" star core can be constructed using two trifunctional elements and a short cross bar.

The simplest method is to extensively transesterify polyethylene terephthalate ester to a high proportion of bis (hydroxyethyl) terephthalate using excess ethanediol then rapidly evaporating the excess ethanediol from the mixture. This produces mainly monomer and dimer. The product is then reacted with trimellitic anhydride to give esterification of the hydroxyl groups of the short oligimers, to give the simplest star core A.

Product A is reacted with ethanediol to esterify the carboxylic acid groups to produce star core B.

Alternatively, A can be treated with acetic anhydride to convert the carboxylic acid groups to mixed acid anhydride groups to give the star core C.

"C" is then reacted with ethanediol to give star core D which has fewer tri-star cores as a by-product.

Alternatively, the trimellitic anhydride can be reacted with ethanediol directly to give only an ethylene crossbar. This is best performed in two steps: the first step with an inert solvent for the ethanediol where the trimellitic anhydride reacts and the solvent is then removed, followed by the second step; where the free carboxylic acid groups are esterified with ethanediol to give tetra star core D.

Finally, isophthalic acid may be reacted exhaustively with acetic anhydride to produce the "I" core, E, as a mixed acetic anhydride.

Persons skilled in the art will understand that each of the cores A, B, C, D and E will have different proportions of bi-star, tri-star and tetra star and a different cost of production. Each star core will form a core in the polycondensation stage reactor where it will react with the linear polymers present to give a significant proportion of "H" polymer or "Y" polymer (if it has a high proportion of tri-star). Further the addition of the additive can be delayed in the polycondensation to prevent transesterification of the crossbars to form "Y" polymer.

It has also been found that the tetra star core can be produced by reacting "cyclohexane dimethanol" with trimellitic anhydride. The ester bonds produced are more stable than with ethanediol and do not generate yellow byproducts to the same degree.

EXAMPLES

The invention will now be further explained and illustrated with reference to the following non-limiting examples.

Examples 1 to 5 relate to the second aspect of the invention. The first three examples are directed to the production of "H" star cores, the fourth example is directed to the production of "Y" star polymers and the fifth example to "I" star polymers.

Examples 6 to 12 relate to the production of high molecular weight polymers from star cores according to the first aspect of the invention.

Example 1

Trimellitic anhydride (192 g) and cyclohexane dimethanol (72 g) are intimately mixed and heated to 140° C. over one hour then maintained at this temperature for three hours. The product is cooled and crushed to give the tetra carboxylic acid core A. The product A (132 g) is then mixed with acetic acid anhydride at ambient temperature for 10 hours to cause dissolution, then heated to 100° C. for two hours and the by-product acetic acid removed slowly under vacuum to give the mixed anhydride core (B). "B" is then reacted with 5 moles of ethanediol at 160° C. for one hour then the excess ethanediol removed under vacuum to give the ester core (C).

Example 2

Trimellitic anhydride (192 g) and ethanediol (35 g) are intimately mixed and heated to 140° C. over one hour then maintained at temperature for three hours. The product is cooled and crushed to give the tetra carboxylic acid core (A1). The product (A1) (132 g) is then mixed with acetic acid anhydride at ambient temperature for 10 hours to cause dissolution, then heated to 100° C. for two hours and the by-product acetic acid removed slowly under vacuum to give the mixed anhydride core (B1). "B1" is then reacted with 5 moles of ethanediol at 160° C. for one hour then the excess ethanediol removed under vacuum to give the ester core (C1).

Example 3

Trimellitic anhydride (192 g) and bis(hydroxyethyl) terephthalate (72 g) are intimately mixed and heated to 140° C. over one hour then maintained at temperature for three hours. The product is cooled and crushed to give the tetra carboxylic acid core (A2). The product (A2) (132 g) is then mixed with acetic acid anhydride at ambient temperature for 10 hours to cause dissolution, then heated to 100° C. for two hours and the by-product acetic acid removed slowly under vacuum to give the mixed anhydride core (B2). "B2" is then reacted with 5 moles of ethanediol at 160° C. for one hour then the excess ethanediol removed under vacuum to give the ester core (C2).

Example 4

Trimellitic anhydride (96 g) is mixed with acetic acid anhydride at ambient temperature for 10 hours to cause dissolution, then heated to 100° C. for two hours and the by-product acetic acid removed slowly under vacuum to give the mixed anhydride core (B3). "B3" is then reacted with 5 moles of ethanediol at 160° C. for one hour then the excess ethanediol removed under vacuum to give the ester core (C3).

This reaction can be represented by the following equation:

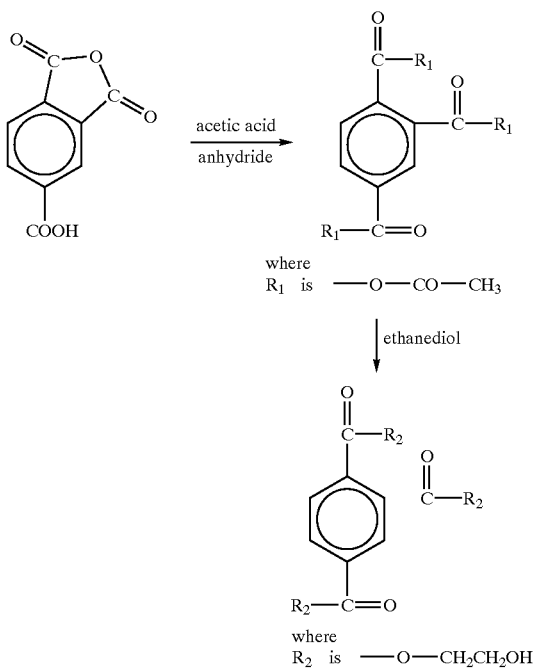

Example 5

50 grams of isophthalic acid were treated with 250 milliliters of acetic anhydride, 1.25 grams of zinc acetate and 0.25 gram of anhydrous oxalic acid at 80° C. for two hours under nitrogen blanket, allowing slow evaporation of approximately half of the acetic anhydride. Three further additions of 0.25 gram of oxalic acid with replacement of the evaporated acetic anhydride, taking eight hours in total. Finally the excess acetic anhydride was removed to give the bi-functional core (E).

Example 6

A batch of molten linear PET polymers was prepared by the masterbatch technique with 250 ppm germanium oxide catalyst. The stirrer torque indicated that the product had an intrinsic viscosity of 0.57 dl/g and temperature of 285° C. To the melt was added 2 g/kg of core "A" as a fine powder. Immediately the viscosity began to increase at the rate of 0.072 dl/(g.hr). The reaction was stopped after 45 minutes and the high molecular weight PET polymer product extruded and granulated.

Example 7

A batch of molten linear PET polymers was prepared by the masterbatch technique with 250 ppm germanium oxide catalyst. The stirrer torque indicated that the product had an intrinsic viscosity of 0.63 dl/g and temperature of 285° C. To the melt was added 3 g/kg of core "C1" as a viscous liquid. Immediately the viscosity began to increase at the rate of 0.3 dl/(g.hr). The reaction was stopped after 30 minutes and the high molecular weight PET product extruded and granulated. Yellow by-products only gave an increase of b=0.7 during the star reaction.

Example 8

A compounding extruder was arranged as a source of molten linear PET polymers with a retention time of 3 minutes and product temperature of 307° C. The extruded product was conventionally cooled in a water bath then granulated. A sample with no additive was produced then core "B" was added at 0.1 mole %, causing an increase in melt viscosity corresponding to a 4 times increase in the apparent weight average molecular weight and an increase of b=0.5.

Example 9

A compounding extruder was arranged as a source of molten linear PET polymers with a retention time of 3 minutes and product temperature of 307° C. The extruded product was cooled in a water bath then granulated. A sample with no additive was produced then core "B3" was added at 0.1 mole %, causing an increase in melt viscosity corresponding to a 3 times increase in the apparent weight average molecular weight, and an increase of b=0.7.

Example 10

A compounding extruder was arranged as a source of molten linear PET polymer with a retention time of 4.75 minutes and product temperature of 307° C. The extruded product was conventionally cooled in a water bath then granulated. A sample with no additive was produced then core "B" was added at 0.1 mole %, causing an increase in melt viscosity corresponding to a 4 times increase in the apparent weight average molecular weight, and an increase in b=0.5.

Example 11

A compounding extruder was arranged as a source of molten linear PET polymer with a retention time of 4.75 minutes and product temperature of 307° C. The extruded product was conventionally cooled in a water bath then granulated. A sample with no additive was produced then core "E" was added at 0.1 mole %, causing an increase in melt viscosity corresponding to a 3 times increase in the apparent weight average molecular weight, and an increase in b=0.5.

Example 12

An extruder was arranged as a source of molten linear PET polymers at a temperature of 285° C. and piped into a swept surface evaporator with a surface temperature of 290° C. and a pressure of 100 Pa., and a retention time of 4 minutes. The product was cooled and granulated giving a control. Then the molten polymer was again introduced into the reactor and simultaneously molten core E was metered into the evaporator at 0.07 mole %. The action of the blades was used to mix the components and evaporate the acetic acid by-product. The polymer was retained in the evaporation zone for 4 minutes then withdrawn and conventionally cooled in a water bath then granulated. Comparison of control and additive treated products showed increase in melt viscosity corresponding to a 2.5 times increase in the apparent weight average molecular weight and an increase in b=04. It will be understood by persons skilled in the art that the products produced by the processes covered by this invention would be suitable for stretch blow moulding.

Persons skilled in the art would understand that many equipment types could be used to perform the required operations. It will further be understood by persons skilled in the art that the "H" form will in general not be symmetrical but instead will follow the distribution of oligimers found in feed polymer melts at the finishing stage. Similarly, the stem and branches of the "Y" form will not necessarily be of the same length. It will be understood that the use of the symbols "I", "H" and "Y" throughout this specification have been intended to include symmetrical and all asymmetrical forms of "I", "H" and "Y".

The word 'comprising' and forms of the word 'comprising' as used in this description and in the claims does not limit the invention claimed to exclude any variants or additions.

Other advantages and modifications to the invention as described above will be apparent to those skilled in the art and all such modifications and adaptations are included in the scope of the invention.

What is claimed is:

1. A process for producing a high molecular weight polyester comprising reacting one or more preformed linear polyesters with at least 0.07 mole % of one or more cores to form high molecular weight polyesters; wherein the preformed linear polyesters are at a temperature in the range from the melting point of said preformed linear polyesters to 330° C.; and wherein the cores are selected from the group consisting of:

(i) a compound of the formula:

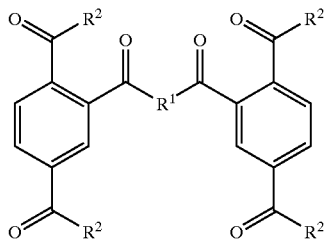

wherein
$R^1$ is —OCH$_2$CH$_2$O—,

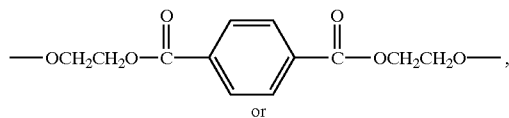

or

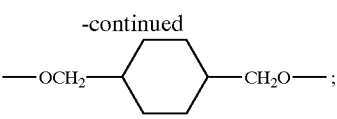

and
$R^2$ is —OH, —OCOCH$_3$, —OCH$_2$CH$_2$OH;

(ii) a compound of the formula:

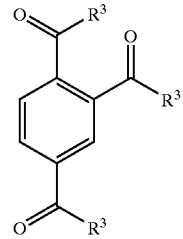

wherein
$R^3$ is —OCOCH$_3$ or —OCH$_2$CH$_2$OH (iii) a compound of the formula:

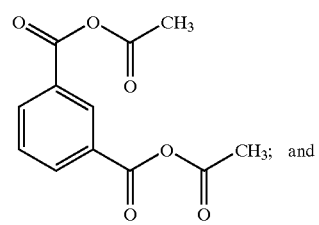

and (iv) a mixture thereof.

2. The process according to claim 1, wherein said reaction is conducted at a reduced pressure.

3. The process according to claim 1, wherein the reaction temperature is at least 270° C.

4. The process according to claim 3, wherein the reaction temperature is about 280° C.

5. The process according to claim 1, wherein the reaction time is less than ten minutes.

6. The process according to claim 1, wherein the preformed linear polyester is a polyethylene terephthalate polymer.

7. The process according to claim 1, wherein said core compound comprises a mixed anhydride reactive group.

8. The process according to claim 1, wherein the core is the acetic acid anhydride of isophthalic acid.

9. A star core for use in the preparation of a high molecular weight polymer, wherein said star core is a mixed anhydride of the formula:

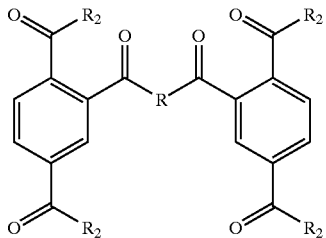

wherein $R_2$ is —O—C(=O)—CH$_3$; and
R is
,
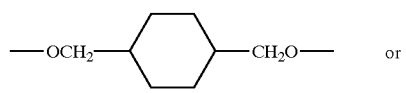 or
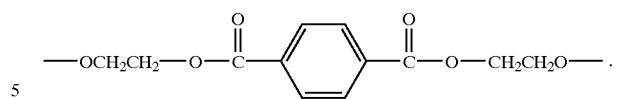.
* * * * *